United States Patent
Fujii et al.

(10) Patent No.: US 9,783,821 B2
(45) Date of Patent: Oct. 10, 2017

(54) CELL FOR USE IN IMMUNOTHERAPY WHICH CONTAINS MODIFIED NUCLEIC ACID CONSTRUCT ENCODING WILMS TUMOR GENE PRODUCT OR FRAGMENT THEREOF, METHOD FOR PRODUCING SAID CELL, AND SAID NUCLEIC ACID CONSTRUCT

(75) Inventors: Shin-ichiro Fujii, Yokohama (JP); Kanako Shimizu, Yokohama (JP); Jun Shinga, Yokohama (JP)

(73) Assignee: RIKEN, Saitama (JP)

( * ) Notice: Subject to any disclaimer, the term of this patent is extended or adjusted under 35 U.S.C. 154(b) by 366 days.

(21) Appl. No.: 14/235,333

(22) PCT Filed: Jul. 30, 2012

(86) PCT No.: PCT/JP2012/069377
§ 371 (c)(1),
(2), (4) Date: Jan. 27, 2014

(87) PCT Pub. No.: WO2013/018778
PCT Pub. Date: Feb. 7, 2013

(65) Prior Publication Data
US 2014/0179004 A1   Jun. 26, 2014

(30) Foreign Application Priority Data

Jul. 29, 2011  (JP) .................. 2011-167796

(51) Int. Cl.
*C12N 15/85* (2006.01)
*A61K 39/00* (2006.01)
*C07K 14/47* (2006.01)
*C07K 14/82* (2006.01)

(52) U.S. Cl.
CPC .......... *C12N 15/85* (2013.01); *A61K 39/0011* (2013.01); *C07K 14/4748* (2013.01); *C07K 14/82* (2013.01); *A61K 2039/5152* (2013.01); *A61K 2039/5156* (2013.01); *C07K 2319/00* (2013.01); *C07K 2319/50* (2013.01)

(58) Field of Classification Search
None
See application file for complete search history.

(56) References Cited

U.S. PATENT DOCUMENTS

| | | |
|---|---|---|
| 2003/0072767 A1 | 4/2003 | Gaiger |
| 2010/0233215 A1 | 9/2010 | Fujii |
| 2011/0190384 A1 | 8/2011 | Sugiyama |
| 2011/0280895 A1 | 11/2011 | Fujii |
| 2013/0189302 A1 | 7/2013 | Fujii |
| 2014/0179004 A1* | 6/2014 | Fujii .................. A61K 39/0011 435/458 |

FOREIGN PATENT DOCUMENTS

| | | |
|---|---|---|
| EP | 2308987 | 4/2011 |
| WO | 2007/097370 | 8/2007 |
| WO | 2007119564 | 10/2007 |
| WO | 2009-046974 | 4/2009 |
| WO | 2010/061930 | 6/2010 |
| WO | 2011/059835 | 5/2011 |

OTHER PUBLICATIONS

European Search Report, European Patent Application No. 12820579.6, mailed Mar. 20, 2015.
Search Report for PCT/JP2012/069377 dated Sep. 4, 2012.
Shastri, N., et al., "Major histocompatibility class I molecules can present cryptic translation products to T-cells", J. Biol. Chem., Jan. 20, 1995, vol. 270, No. 3, pp. 1088-1091.
Ja Kyte et al., "Phase I / II trial of melanoma therapy with dendritic cells transfected with autologous tumor-mRNA", Cancer Gene Therapy, vol. 13 (2006), pp. 905-918.
LJ Mu, et al., "Immunotherapy with allotumour mRNA-transfected dendritic cells in androgen-resistant prostate cancer patients", British Journal of Cancer, vol. 93 (2005), pp. 749-756.
Zhen Su, et al., "Telomerase mRNA-Transfected Dendritic Cells Stimulate Antigen-Specific CD8+ and CD 4+ T Cell Responses in Patients with Metastatic Prostate Cancer", The Journal of Immunology, vol. 174 (2005), pp. 3798-3807.
Axel Heiser, et al., "Autologous dendritic cells transfected with prostate-specific antigen RNA stimulate CTL responses against metastatic prostate tumors", Journal of Clinical Investigation, vol. 109, No. 3, Feb. 2002, pp. 409-417.
Smita K. Nair, et al., "Induction of cytotoxic T cell responses and tumor immunity against unrelated tumors using telomerase reverse transcriptase RNA transfected dendritic cells", Nature Medicine, vol. 6, No. 8, Sep. 2000, pp. 1011-1017.
Condon C., et al., "DNA-based immunization by vivo transfection of dendritic cells", Nat. Med. vol. 2, Oct. 1996, pp. 1122-1128 (Abstract Only).
David Boczkowski et al., "Dendritic Cells Pulsed with RNA are Potent Antigen-presenting Cells in Vitro and in Vivo", J. Exp. Med., vol. 184, Aug. 1996, pp. 465-472.
Jonathan D. Silk, et al., "Utilizing the adjuvant properties of CD1d-dependent NKT cells in T cell-mediated immunotherapy", The Journal of Clinical Investigation, vol. 114, No. 12, Dec. 2004, pp. 1800-1811.
Ian F. Hermans et al., "NKT Cells Enhance CD4+ and CD8+ T cell Responses to Soluble Antigen In Vivo through Direct Interaction with Dendritic Cells", The Journal of Immunology, vol. 171 (2003), pp. 5140-5147.
Franco Fais, et al., "CD1d is Expressed on B-Chronic Lymphocytic Leukemia Cells and Mediates α-Galactosylceramide Presentation to Natural Killer T Lymphocytes", Int. J. Cancer, vol. 109 (2004), pp. 402-411.

(Continued)

*Primary Examiner* — Michael Burkhart
(74) *Attorney, Agent, or Firm* — Casimir Jones, SC

(57) ABSTRACT

A cell of the present invention contains a nucleic acid construct encoding a WT1 gene product or a fragment of the WT1 gene product. The nucleic acid construct contains (i) a region encoding a desired fragment of the WT1 gene product and (ii) only AUG as a functional start codon. The present invention can provide a cell into which the nucleic acid construct is introduced so that an expression level of a WT1 gene product or a fragment of the WT1 gene product is remarkably enhanced.

7 Claims, 1 Drawing Sheet

(56) References Cited

OTHER PUBLICATIONS

Leonid S. Metelitsa et al., "Human NKT Cells Mediate Antitumor Cytotoxicity Directly by Recognizing Target Cell CD1d with Bound Ligand or Indirectly by Producing IL-2 to Activate NK Cells", The Journal of Immunology, vol. 167 (2001), pp. 3114-3122.

Shin-ichiro, Fujii, et al., "Detection and activation of human Vα24+ natural killer T cells using α-galactosyl ceramide-pulsed dendritic cells", Journal of Immunological Methods, vol. 272 (2003), pp. 147-159.

Shin-ichiro, Fujii et al., "The Linkage of Innate to Adaptive Immunity via Maturing Dendritic Cells In Vivo Requires CD40 Ligation in Addition to Antigen Presentation and CD80/86 Costimulation", J. Exp. Med., vol. 199, No. 12, Jun. 21, 2004, pp. 1607-1618.

Shin-ichiro, Fujii, et al., "Activation of Natural Killer T Cells by α-Galactosylceramide Rapidly Induces the Full Maturation of Dendritic Cells In Vivo and Thereby Acts as an Adjuvant for Combined CD4 and CD8 T Cell Immunity to a Coadministered Protein", J. Exp. Med., vol. 198, No. 2, Jul. 21, 2003, pp. 267-279.

Shin-ichiro, Fujii, et al., "Prolonged IFN-y-producing NKT response induced with α-galactosylceramide-loaded DCs", Nature Immunology, vol. 3, No. 9, Sep. 2002, pp. 867-874.

English translation of the International Preliminary Report on Patentability (Chapter 1) of PCT Application No. PCT/JP2012/069377 dated Feb. 13, 2014.

Bruening, W. & Pelletier, J. et al., "A non-AUG translational initiation event generates novel WT1 isoforms", The Journal of Biological Chemistry, 1996, vol. 271, No. 15, pp. 8646-8654.

Office Action for Australian Patent Application No. 2012291101, mailed Feb. 27, 2015.

\* cited by examiner

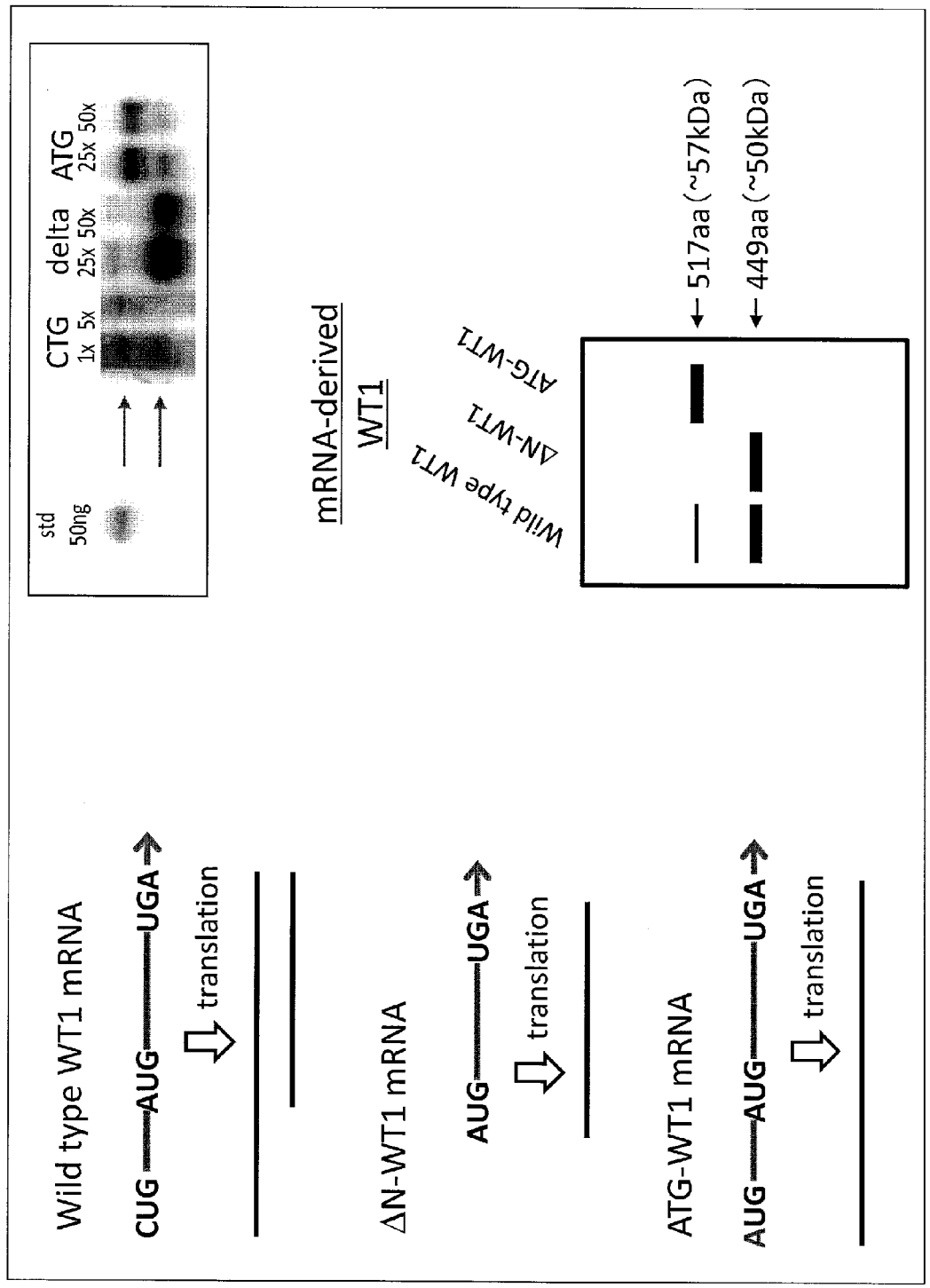

SEQUENCE LISTING

```
<160> NUMBER OF SEQ ID NOS: 9

<210> SEQ ID NO 1
<211> LENGTH: 517
<212> TYPE: PRT
<213> ORGANISM: Homo sapiens

<400> SEQUENCE: 1

Met Gln Asp Pro Ala Ser Thr Cys Val Pro Glu Pro Ala Ser Gln His
1               5                   10                  15

Thr Leu Arg Ser Gly Pro Gly Cys Leu Gln Gln Pro Glu Gln Gln Gly
            20                  25                  30

Val Arg Asp Pro Gly Gly Ile Trp Ala Lys Leu Gly Ala Ala Glu Ala
        35                  40                  45

Ser Ala Glu Arg Leu Gln Gly Arg Arg Ser Arg Gly Ala Ser Gly Ser
    50                  55                  60

Glu Pro Gln Gln Met Gly Ser Asp Val Arg Asp Leu Asn Ala Leu Leu
65                  70                  75                  80

Pro Ala Val Pro Ser Leu Gly Gly Gly Gly Cys Ala Leu Pro Val
                85                  90                  95

Ser Gly Ala Ala Gln Trp Ala Pro Val Leu Asp Phe Ala Pro Pro Gly
                100                 105                 110

Ala Ser Ala Tyr Gly Ser Leu Gly Gly Pro Ala Pro Pro Pro Ala Pro
            115                 120                 125

Pro Pro Pro Pro Pro Pro Pro His Ser Phe Ile Lys Gln Glu Pro
        130                 135                 140

Ser Trp Gly Gly Ala Glu Pro His Glu Glu Gln Cys Leu Ser Ala Phe
145                 150                 155                 160

Thr Val His Phe Ser Gly Gln Phe Thr Gly Thr Ala Gly Ala Cys Arg
                165                 170                 175

Tyr Gly Pro Phe Gly Pro Pro Pro Ser Gln Ala Ser Ser Gly Gln
            180                 185                 190

Ala Arg Met Phe Pro Asn Ala Pro Tyr Leu Pro Ser Cys Leu Glu Ser
            195                 200                 205

Gln Pro Ala Ile Arg Asn Gln Gly Tyr Ser Thr Val Thr Phe Asp Gly
    210                 215                 220

Thr Pro Ser Tyr Gly His Thr Pro Ser His His Ala Ala Gln Phe Pro
225                 230                 235                 240

Asn His Ser Phe Lys His Glu Asp Pro Met Gly Gln Gln Gly Ser Leu
                245                 250                 255

Gly Glu Gln Gln Tyr Ser Val Pro Pro Pro Val Tyr Gly Cys His Thr
            260                 265                 270

Pro Thr Asp Ser Cys Thr Gly Ser Gln Ala Leu Leu Leu Arg Thr Pro
        275                 280                 285

Tyr Ser Ser Asp Asn Leu Tyr Gln Met Thr Ser Gln Leu Glu Cys Met
    290                 295                 300
```

-continued

```
Thr Trp Asn Gln Met Asn Leu Gly Ala Thr Leu Lys Gly Val Ala Ala
305                 310                 315                 320
Gly Ser Ser Ser Ser Val Lys Trp Thr Glu Gly Gln Ser Asn His Ser
            325                 330                 335
Thr Gly Tyr Glu Ser Asp Asn His Thr Thr Pro Ile Leu Cys Gly Ala
        340                 345                 350
Gln Tyr Arg Ile His Thr His Gly Val Phe Arg Gly Ile Gln Asp Val
    355                 360                 365
Arg Arg Val Pro Gly Val Ala Pro Thr Leu Val Arg Ser Ala Ser Glu
370                 375                 380
Thr Ser Glu Lys Arg Pro Phe Met Cys Ala Tyr Pro Gly Cys Asn Lys
385                 390                 395                 400
Arg Tyr Phe Lys Leu Ser His Leu Gln Met His Ser Arg Lys His Thr
                405                 410                 415
Gly Glu Lys Pro Tyr Gln Cys Asp Phe Lys Asp Cys Glu Arg Arg Phe
            420                 425                 430
Ser Arg Ser Asp Gln Leu Lys Arg His Gln Arg Arg His Thr Gly Val
        435                 440                 445
Lys Pro Phe Gln Cys Lys Thr Cys Gln Arg Lys Phe Ser Arg Ser Asp
    450                 455                 460
His Leu Lys Thr His Thr Arg Thr His Thr Gly Lys Thr Ser Glu Lys
465                 470                 475                 480
Pro Phe Ser Cys Arg Trp Pro Ser Cys Gln Lys Lys Phe Ala Arg Ser
                485                 490                 495
Asp Glu Leu Val Arg His His Asn Met His Gln Arg Asn Met Thr Lys
            500                 505                 510
Leu Gln Leu Ala Leu
        515

<210> SEQ ID NO 2
<211> LENGTH: 3037
<212> TYPE: RNA
<213> ORGANISM: Homo sapiens

<400> SEQUENCE: 2
agcuggggua aggaguucaa ggcagcgccc acacccgggg gcucuccgca acccgaccgc      60 cguccgcuc  cccacuuucc cgccuccccu cccaccuacu cauucaccca cccacccacc    120
cagagccggg acggcagccc aggcgcccgg gccccgccgu cuccucgccg cgauccugga    180
cuuccucuug cugcaggacc cggcuuccac gugugucccg gagccggcgu cucagcacac    240
gcuccgcucc gggccugggu gccuacagca gccagagcag cagggagucc gggacccggg    300
cggcaucugg gccaaguuag cgccgccga  ggccagcgcu gaacgucucc agggccggag    360
gagccgcggg gcguccgggu cugagccgca gcaaauggc  uccgacgugc gggaccugaa    420
cgcgcugcug cccgccgucc ccucccuggg uggcggcggc ggcugugccc ugccugugag    480
cggcgcggcg caguggggcgc cggugcugga cuuugcgccc ccgggcgcuu cggcuuacgg    540
gucguugggc ggcccgcgc  cgccaccggc uccgccgcca ccccgccgc  cgccgccuca    600 cuccuucauc aaacaggagc cgagcugggg cggcgcggag ccgcacgagg agcagugccu    660
gagcgccuuc acuguccacu uuccggcca  guucacuggc acagccggag ccugucgcua    720
cgggcccuuc gguccuccuc cgcccagcca ggcgucaucc ggcaggcca  ggauguuucc    780 uaacgcgccc uaccgcccca gcugccucga gagccagccc gcuauucgca aucagggaua    840
cagcacgguc accuucgacg ggacgcccag cuacggucac acgcccucgc accaugcggc    900
```

-continued

```
gcaguucccc aaccacucau ucaagcauga ggaucccaug ggccagcagg gcucgcuggg    960
ugagcagcag uacucggugc cgcccccggu cuauggcugc cacaccccca ccgacagcug   1020
caccggcagc caggcuuugc ugcugaggac gcccuacagc agugacaauu uauaccaaau   1080
gacaucccag cuugaaugca ugaccuggaa ucagaugaac uuaggagcca ccuuaaaggg   1140
aguugcugcu gggagcucca gcucagugaa auggacagaa gggcagagca accacagcac   1200 agggacgag agcgauaacc acacaacgcc cauccucugc ggagcccaau acagaauaca   1260
```

<400> SEQUENCE: 3

```
agctggggta aggagttcaa ggcagcgccc acacccgggg gctctccgca acccgaccgc      60
ctgtccgctc ccccacttcc cgccctccct cccacctact cattcaccca cccacccacc     120
cagagccggg acggcagccc aggcgccggg gccccgccgt ctcctcgccg cgatcctgga     180
cttcctcttg ctgcaggacc cggcttccac gtgtgtcccg gagccggcgt ctcagcacac     240
gctccgctcc gggcctgggt gcctacagca gccagagcag cagggagtcc gggacccggg     300
cggcatctgg gccaagttag cgccgccga ggccagcgct gaacgtctcc agggccggag      360
gagccgcggg gcgtccgggt ctgagccgca gcaaatgggc tccgacgtgc gggacctgaa     420
cgcgctgctg cccgccgtcc cctccctggg tggcggcggc ggctgtgccc tgcctgtgag     480
cggcgcggcg cagtgggcgc cggtgctgga ctttgcgccc ccgggcgctt cggcttacgg     540
gtcgttgggc ggccccgcgc cgccaccggc tccgccgcca ccccgccgc cgccgcctca      600
ctccttcatc aaacaggagc cgagctgggg cggcgcggag ccgcacgagg agcagtgcct     660
gagcgccttc actgtccact tttccggcca gttcactggc acagcggag cctgtcgcta      720
cgggcccttc ggtcctcctc cgcccagcca ggcgtcatcc ggccaggca ggatgtttcc      780
taacgcgccc tacctgccca gctgcctcga gagccagccc gctattcgca atcagggtta     840
cagcacggtc accttcgacg ggacgccag ctacggtcac acgccctcgc accatgcggc      900
gcagttcccc aaccactcat tcaagcatga ggatcccatg gccagcagg gctcgctggg     960
tgagcagcag tactcggtgc cgccccggt ctatggctgc cacacccca ccgacagctg      1020
caccggcagc caggcttgc tgctgaggac gccctacagc agtgacaatt tataccaaat     1080
gacatcccag cttgaatgca tgacctggaa tcagatgaac ttaggagcca ccttaaaggg    1140
agttgctgct gggagctcca gctcagtgaa atggacagaa gggcagagca accacagcac    1200
agggtacgag agcgataacc acacaacgcc catcctctgc ggagcccaat acagaataca    1260
cacgcacggt gtcttcagag gcattcagga tgtgcgacgt gtgcctggag tagccccgac    1320
tcttgtacgg tcggcatctg agaccagtga gaaacgcccc ttcatgtgtg cttacccagg    1380
ctgcaataag agatatttta gctgtcccca cttacagatg cacagcagga agcacactgg    1440
tgagaaacca taccagtgtg acttcaagga ctgtgaacga aggttttctc gttcagacca    1500
gctcaaaaga caccaaagga gacatacagg tgtgaaacca ttccagtgta aaacttgtca    1560
gcgaaagttc tcccggtccg accacctgaa gacccacacc aggactcata caggtaaaac    1620
aagtgaaaag cccttcagct gtcggtggcc aagttgtcag aaaaagtttg cccggtcaga    1680
tgaattagtc cgccatcaca acatgcatca gagaaacatg accaaactcc agctggcgct    1740
ttgaggggtc tccctcgggg accgttcagt gtcccaggca gcacagtgtg tgaactgctt    1800
tcaagtctga ctctccactc ctcctcacta aaaaggaaac ttcagttgat cttcttcatc    1860
caacttccaa gacaagatac cggtgcttct ggaaactacc aggtgtgcct ggaagagttg    1920
gtctctgccc tgcctacttt tagttgactc acaggccctg gagaagcagc taacaatgtc    1980
tggttagtta aaagcccatt gccatttggt gtggattttc tactgtaaga agagccatag    2040
ctgatcatgt ccccctgacc cttccttct tttttatgc tcgttttcgc tggggatgga     2100
attattgtac cattttctat catggaatat ttataggcca gggcatgtgt atgtgtctgc    2160
taatgtaaac tttgtcatgg tttccatta ctaacagcaa cagcaagaaa taaatcagag     2220
agcaaggcat cggggtgaa tcttgtctaa cattcccgag gtcagccagg ctgctaacct     2280
ggaaagcagg atgtagttct gccaggcaac ttttaaagct catgcatttc aagcagctga    2340
```

```
agaaaaaatc agaactaacc agtacctctg tatagaaatc taaaagaatt ttaccattca      2400
gttaattcaa tgtgaacact ggcacactgc tcttaagaaa ctatgaagat ctgagatttt      2460
tttgtgtatg ttttttgactc ttttgagtgg taatcatatg tgtctttata gatgtacata    2520
```
```
tttgtgtatg tttttgactc ttttgagtgg taatcatatg tgtctttata gatgtacata     2520
cctccttgca caaatggagg ggaattcatt ttcatcactg ggagtgtcct tagtgtataa     2580
aaaccatgct ggtatatggc ttcaagttgt aaaaatgaaa gtgactttaa aagaaaatag     2640
gggatggtcc aggatctcca ctgataagac tgttttttaag taacttaagg acctttgggt    2700
ctacaagtat atgtgaaaaa aatgagactt actgggtgag gaaatccatt gtttaaagat     2760
ggtcgtgtgt gtgtgtgtgt gtgtgtgtgt gtgtgtgttg tgttgtgttt tgtttttttaa   2820 gggagggaat ttattattta ccgttgcttg aaattactgt gtaaatatat gtctgataat    2880
gatttgctct ttgacaacta aaattaggac tgtataagta ctagatgcat cactgggtgt    2940
tgatcttaca agatattgat gataacactt aaaattgtaa cctgcatttt tcactttgct   3000
ctcaattaaa gtctattcaa aaggaaaaaa aaaaaaa                              3037

<210> SEQ ID NO 4
<211> LENGTH: 1551
<212> TYPE: RNA
<213> ORGANISM: Homo sapiens

<400> SEQUENCE: 4
augcaggacc cggcuuccac guguguccccg agccggcgu ucagcacac gcuccgcucc       60 gggccugggu gccuacagca gccagagcag cagggagucc gggacccggg cggcaucugg     120
gccaaguuag gcgccgccga ggccagcgcu gaacgucucc agggccggag gagccgcggg    180
gcguccgggu cugagccgca gcaaaugggc uccgacgugc gggaccugaa cgcgcugcug    240
cccgccgucc ccucccuggg uggcggcggc ggcugugccc ugccugugag cggcgcggcg    300
cagugggcgc cggugcugga cuuugcgccc ccggggcgcuu cggcuuacgg gucguugggc    360
ggccccgcgc cgccaccggc uccgccgcca ccccgccgc cgccgccuca cuccuucauc     420
aaacaggagc cgagcugggg cggcgcggag ccgcacgagg agcagugccu gagcgccuuc    480
acuguccacu uuccggccaa guucacuggc acagccggag ccugucgcua cgggccccuuc   540 ggucccccuc cgcccagcca ggcgucaucc ggcgucauccc ggcaggcca ggauguuuccc   600
```
(continuing)
```
ggucccccuc cgcccagcca ggcgucaucc ggcaggcca ggauguuuccc uaacgcgccc    600 uaccugccca gcugccucga gagccagccc gcuauucgca aucaggguua cagcacgguc    660
accuucgacg ggacgcccag cuacggucac acgcccucgc accaugcggc gcaguuccccc   720 aaccacucau ucaagcauga ggaucccaug ggccagcagg gcucgcuggg ugagcagcag    780
uacucggugc cgcccccggu cuauggcugc cacacccca ccgacagcug caccggcagc     840
caggcuuugc ugcugaggac gcccuacagc agugacaauu uauaccaaau gacaucccag    900
cuugaaugca ugaccuggaa ucagaugaac uuaggagcca ccuuaaaggg aguugcugcu    960
gggagcucca gcucagugaa auggacagaa gggcagagca ccacagcac agguacgag     1020 agcgauaacc acacaacgcc cauccucugc ggagcccaau acagaauaca cacgcacggu    1080
gucuucagag gcauucagga ugugcgacgu gugccuggag uagccccgac ucuuguacgg    1140
ucggcaucug agaccaguga gaacgcccc uucaugugug cuuacccagg cugcaauaag     1200
agauauuuua agcugucccca cuuacagaug cacagcagga agcacacugg ugagaaacca   1260
uaccagugug acuucaagga cugugaacga agguuuucuc guucagacca gcucaaaaga   1320
caccaaagga gacauacagg ugugaaacca uuccagugua aaacuuguca gcgaaaguuc    1380
```

| | | | | |
|---|---|---|---|---|
| ucccgguccg | accaccugaa | gacccacacc | aggacucaua | cagguaaaac  aagugaaaag  1440 |
| cccuucagcu | gucgguggcc | aaguugucag | aaaaaguuug | cccggucaga  ugaauuaguc  1500 |
| cgccaucaca | acaugcauca | gagaaacaug | accaaacucc | agcuggcgcu  u            1551 |

<210> SEQ ID NO 5
<211> LENGTH: 1347
<212> TYPE: RNA
<213> ORGANISM: Homo sapiens

<400> SEQUENCE: 5

| | | | | | |
|---|---|---|---|---|---|
| augggcuccg | acgugcggga | ccugaacgcg | cugcugcccg | ccgucccuc  ccugggugge  | 60 |
| ggcggcggcu | gugcccugcc | ugugagcggc | gcggcgcagu | gggcgccggu  gcuggacuuu  | 120 |
| gcgcccccgg | gcgcuucggc | uuacgggucg | uugggcggcc | ccgcgccgcc  accggcuccg  | 180 |
| ccgccacccc | cgccgccgcc | gccucacucc | uucaucaaac | aggagccgag  cuggggcggc  | 240 |
| gcggagccgc | acgaggagca | gugccugagc | gccuucacug | uccacuuuuc  cggccaguuc  | 300 |
| acuggcacag | ccggagccug | ucgcuacggg | cccuucgguc | ucccuccgcc  cagccaggcg  | 360 |
| ucauccggcc | aggccaggau | guuuccuaac | gcgcccuacc | ugccagcug  ccucgagagc  | 420 |
| cagcccgcua | uucgcaauca | ggguuacagc | acggucaccu | cgacgggac  gcccagcuac  | 480 |
| ggucacacgc | ccucgcacca | ugcggcgcag | uuccccaacc | acucauucaa  gcaugaggau  | 540 |
| cccaugggc | agcagggcuc | gcugggugag | cagcaguacu | cggugccgcc  cccggucuau  | 600 |
| ggcugccaca | ccccaccga | cagcugcacc | ggcagccagg | cuuugcugcu  gaggacgccc  | 660 |
| uacagcagug | acaauuuaua | ccaaaugaca | ucccagcuug | aaugcaugac  cuggaaucag  | 720 |
| augaacuuag | gagccaccuu | aaagggaguu | gcugcuggga | gcuccagcuc  agugaaaugg  | 780 |
| acagaagggc | agagcaacca | cagcacaggg | uacgagagcg | auaaccacac  aacgcccauc  | 840 |
| cucugcggag | cccaauacag | aauacacacg | cacggugucu | ucagaggcau  ucaggaugug  | 900 |
| cgacgugugc | cuggaguagc | cccgacucuu | guacggucgg | caucugagac  cagugagaaa  | 960 |
| cgccccuuca | ugugugcuua | cccaggcugc | aauaagagau | auuuuaagcu  gucccacuua  | 1020 |
| cagaugcaca | gcaggaagca | cacuggugag | aaaccauacc | agugugacuu  caaggacugu  | 1080 |
| gaacgaaggu | uuucucguuc | agaccagcuc | aaaagacacc | aaaggagaca  uacaggugug  | 1140 |
| aaaccauucc | aguguaaaac | uugucagcga | aaguucuccc | gguccgacca  ccugaagacc  | 1200 |
| cacaccagga | cucauacagg | uaaaacaagu | gaaaagcccu | ucagcugucg  guggccaagu  | 1260 |
| ugucagaaaa | aguuugcccg | gucagaugaa | uuagccgcc | aucacaacau  gcaucagaga  | 1320 |
| aacaugacca | aacuccagcu | ggcgcuu    | | | 1347 |

<210> SEQ ID NO 6
<211> LENGTH: 34
<212> TYPE: DNA
<213> ORGANISM: Artificial Sequence
<220> FEATURE:
<223> OTHER INFORMATION: Synthetic primer

<400> SEQUENCE: 6
ccaagcttcc accatgcagg acccggcttc cacg                              34

<210> SEQ ID NO 7
<211> LENGTH: 31
<212> TYPE: DNA
<213> ORGANISM: Artificial Sequence
<220> FEATURE:
<223> OTHER INFORMATION: Synthetic primer

```
<400> SEQUENCE: 7
cggaattctc aaagcgccag ctggagtttg g                              31

<210> SEQ ID NO 8
<211> LENGTH: 33
<212> TYPE: DNA
<213> ORGANISM: Artificial Sequence
<220> FEATURE:
<223> OTHER INFORMATION: Synthetic primer

<400> SEQUENCE: 8
ccaagcttcc accatgggct ccgacgtgcg gga                            33

<210> SEQ ID NO 9
<211> LENGTH: 31
<212> TYPE: DNA
<213> ORGANISM: Artificial Sequence
<220> FEATURE:
<223> OTHER INFORMATION: Synthetic primer

<400> SEQUENCE: 9
cggaattctc aaagcgccag ctggagtttg g                              31
```

CELL FOR USE IN IMMUNOTHERAPY WHICH CONTAINS MODIFIED NUCLEIC ACID CONSTRUCT ENCODING WILMS TUMOR GENE PRODUCT OR FRAGMENT THEREOF, METHOD FOR PRODUCING SAID CELL, AND SAID NUCLEIC ACID CONSTRUCT

CROSS-REFERENCE TO RELATED APPLICATIONS

This application is a national stage of International (PCT) Patent Application Serial No. PCT/JP2012/069377, filed Jul. 30, 2012, which claims the benefit of and priority to JP Patent Application No. 2011-167796 filed Jul. 29, 2011, the contents of which are hereby incorporated by reference for all purposes.

TECHNICAL FIELD

The present invention relates to a nucleic acid construct encoding a Wilms tumor gene product or a fragment of the Wilms tumor gene product. The present invention further relates to a cell into which the nucleic acid construct is introduced so that an expression level of the Wilms tumor gene product or the fragment of the Wilms tumor gene product is remarkably enhanced therein.

BACKGROUND ART

Antitumor effects of an NKT cell which have been known so far include (i) a direct effect on a tumor and (ii) an indirect effect on a tumor via maturation of a dendritic cell (adjuvant effect). As an immunotherapy using the NKT cell, an immunotherapy involving administration of a dendritic cell presenting a tumor antigen has been known, and studies for clinical application of such the immunotherapy have been conducted (Non-Patent Literatures 1 through 7). Further, an antigen-specific immunotherapy using a dendritic cell into which mRNA encoding a tumor antigen is introduced has been already established and clinically applied (Non-Patent Literatures 8 through 15). In order to introduce, into a cell material to be used, an antigen for immune induction in such immunotherapies, it is simple and easy to use an expression vector or the like. However, in a case where the expression vector is introduced into the cell in such an immunotherapy, that immunotherapy may be regarded as a gene therapy and application range thereof may be limited due to regulations. As a measure for avoiding this, introduction of RNA into a dendritic cell has been considered. However, this involves problems of a low introduction efficiency of RNA and a low expression level of a tumor antigen in the dendritic cell. In order to improve therapeutic effects of these immunotherapies, attempts to try various combinations with adjuvants have been made.

Another immunotherapy for a tumor is a peptide therapy involving use of a plurality of epitopes contained in a WT1 protein encoded by a Wilms tumor gene (Wilms tumor 1: WT1).

Meanwhile, the inventors of the subject application have developed unique immunotherapies (Patent Literatures 1, 2, etc.). Disclosed in Patent Literature 1 are (i) an abnormal cell which is isolated from a patient and has, on its surface, CD1d presenting an NKT cell ligand and (ii) a method for producing the cell (Patent Literature 1). This cell is capable of inducing both activation of NKT cells and tumor-specific immune response of T-cells. Disclosed in Patent Literature 2 are (i) an allo-cell which is not derived from a patient and has, on its surface, CD1d presenting an NKT cell ligand and in which a disease-specific antigen is expressed and (ii) a method for producing the cell. This allo-cell is capable of exhibiting immune inducibility similar to that of the cell disclosed in Patent Literature 1 without being isolated from a patient. Such the immunotherapies are expected to be applied to various antitumor immunotherapies for leukemia etc.

CITATION LIST

Patent Literatures

Patent Literature 1
WO 2007/097370 (Publication Date: Aug. 30, 2007)
Patent Literature 2
WO 2010/061930 (Publication Date: Jun. 3, 2007)

Non-Patent Literatures

Non-Patent Literature 1
Nat. Immunol. 3, 867-874 (2002).
Non-Patent Literature 2
J. Immunol. Meth. 272, 147-159 (2003).
Non-Patent Literature 3
J. Exp. Med. 198, 267-279 (2003).
Non-Patent Literature 4
J. Exp. Med. 199, 1607-1618 (2004).
Non-Patent Literature 5
J. Immunol. 167, 3114-3122 (2001).
Non-Patent Literature 6
Int. J. Cancer 109, 402-11 (2004).
Non-Patent Literature 7
J. Immunol. 171, 5140-5147 (2003).
Non-Patent Literature 8
J. Clin. Invest. 114, 1800-11 (2004).
Non-Patent Literature 9
J. Exp. Med. 184:465-472 (1996).
Non-Patent Literature 10
Nat. Med. 2:1122-1128 (1996).
Non-Patent Literature 11
Nat. Med. 6:1011-1017 (2000).
Non-Patent Literature 12
J. Clin. Invest. 109:409-417 (2002).
Non-Patent Literature 13
J. Immunol. 174:3798-3807 (2005).
Non-Patent Literature 14
Br. J. Cancer 93:749-756 (2005).
Non-Patent Literature 15
Cancer Gene Ther. 13:905-918 (2006).

SUMMARY OF INVENTION

Technical Problem

The immunotherapies developed by the inventors of the subject application can improve therapeutic effect in combination with an adjuvant, as with the conventional immunotherapies. However, the inventors of the present invention found that, according to the immunotherapies, a cell itself to be administered is a target to be attacked by an immune system of a patient and accordingly an increase in an expression level of the tumor antigen protein therein greatly contributes to an increase in efficiency of the immune induction. The expression level of the tumor antigen protein is improved by increasing an amount of RNA to be introduced. The improvement in the expression level of the tumor antigen protein in this case is almost proportional to the amount of the RNA to be introduced. However, a total amount of RNA which can be introduced into a cell is limited. Therefore, in a case where, for example, another RNA (such as RNA encoding CD1d) is further introduced into the cell, the expression level of the tumor antigen protein may not be improved to a desired level. In view of this, it is desirable to remarkably enhance the expression level of the tumor antigen protein while suppressing the amount of the RNA to be introduced as much as possible.

In view of the above problem found by the inventors of the present application, an object of the present invention is to remarkably enhance an expression level of a WT1 protein in a cell independently of an expression regulating element contained in an expression vector or the like, in a case where the WT1 protein is selected as a tumor-specific antigenic protein. That is, the object of the present invention is to provide (i) a cell which contains a modified WT1 nucleic acid construct so that an expression level of a WT1-derived polypeptide is enhanced therein independently of DNA and (ii) a modified WT1 nucleic acid construct to be introduced into the cell.

Solution to Problem

The inventors of the present invention found that an expression level of a WT1-derived polypeptide is enhanced far beyond expectations by introducing a mutation into a publicly-known nucleic acid sequence of WT1. Such modified WT1 has not been known so far that allows the remarkable increase in the expression level of the polypeptide. The inventors of the present invention accomplished the present invention as a result of studies based on this finding. Specifically, in order to attain the above object, the present invention includes the following features:

A cell for immunotherapy, including: a nucleic acid construct encoding a Wilms tumor gene product or a fragment of the Wilms tumor gene product, the nucleic acid construct including (i) a region encoding a fragment of the Wilms tumor gene product, the fragment being indicated by positions 194 to 493 of SEQ ID NO: 1 or by positions corresponding to the positions 194 to 493 of a sequence corresponding to SEQ ID NO: 1 and (ii) only one AUG as a functional start codon, connected to a 5' terminal side of the region via 3m (m is 0 or a positive integer) bases intervening between the 5' terminal side of the region and the AUG as the functional start codon.

Advantageous Effects of Invention

According to the present invention, it is possible to provide (i) a cell for immunotherapy into which a nucleic acid construct is introduced so that an expression level of a WT1 gene product or a fragment of the WT1 gene product is enhanced therein independently of an expression regulating element contained in an expression vector or the like and (ii) the nucleic acid construct. Such the cell and nucleic acid construct are applicable to an effective immunotherapy independent of a gene therapy.

BRIEF DESCRIPTION OF DRAWINGS

FIG. 1 is a view illustrating results of assay of proteins from a nucleic acid construct of the present invention for expression levels.

DESCRIPTION OF EMBODIMENTS

Cell for Immunotherapy of the Present Invention

The present invention provides a cell for immunotherapy (hereinafter, simply referred to as a "cell of the present invention") which cell contains a nucleic acid construct encoding a Wilms tumor gene product or a fragment of the Wilms tumor gene product. The nucleic acid construct includes (i) a region encoding a fragment of the Wilms tumor gene product, the fragment being indicated by positions 194 to 493 of SEQ ID NO: 1 or by positions corresponding to the positions 194 to 493 of a sequence corresponding to SEQ ID NO: 1 and (ii) only one AUG as a functional start codon, connected to a 5' terminal side of the region via 3m (m is 0 or a positive integer) bases intervening between the 5' terminal side of the region and the AUG as the functional start codon.

As described later in [Nucleic acid construct of the present invention], introduction of the nucleic acid construct into a cell results in expression of the Wilms tumor gene product or the fragment of the Wilms tumor gene product at a remarkably improved level. Therefore, with the cell for immunotherapy of the present invention, a necessary amount of the cell to be administered to a desired living body in order to attain a large or necessary amount of proteins therein may be small.

The cell of the present invention can be such a dendritic cell that is for immunotherapy including administration of a tumor antigen-presenting dendritic cell and is derived from a living body to which the cell is to be administered. As to the immunotherapy using a dendritic cell, various publicly known literatures can be referred to. Therefore, detailed description of the immunotherapy using a dendritic cell is omitted in the present specification.

Therefore, the following description will discuss a cell particularly preferable as the cell of the present invention. The cell further contains mRNA encoding CD1d, for the purpose of application to the immunotherapies developed by the inventors of the present invention (see WO 2007/097370 and WO 2010/061930). Further, the cell is preferably bound to a glycolipid, recognized by an antigen receptor of an NKT cell, via the CD1 d existing on a surface of the cell. Thus, the glycolipid is presented by the CD1 d on the surface of the cell of the present invention. Therefore, in a case where the cell is administered to a living body, the cell of the present invention is efficiently damaged by an NKT cell. With this damage, the WT1 gene product or the fragment of the WT1 gene product expressed from the nucleic acid construct of the present invention is processed to a peptide fragment. For example, a surrounding dendritic cell takes up the peptide fragment, and then presents to a T cell the peptide fragment and a major histocompatibility antigen (MHC) class II molecule, so that the T cell is activated. At the same time, the NKT cell which has damaged the cell of the present invention is activated by the surrounding dendritic cell which has taken up the peptide fragment. That is, administration of the cell of the present invention causes innate immunity and acquired immunity which is dependent on a tumor-specific antigenic peptide. Thus, the cell of the present invention contains the WT1 gene product or the fragment of the WT1 gene product expressed in a large amount, and therefore can efficiently improve immunity of a living body against a tumor.

The CD1d is an MHC-like molecule which presents a glycolipid as described above. The CD1d is expressed in antigen-presenting cells (such as a dendritic cell) and epithelial cells of specific tissues (such as an intestinal canal and a liver) and in some tumor cells (such as a solid tumor cell and a leukemia cell) and virus-infected cells.

Examples of the glycolipid recognized by the antigen receptor of the NKT cell include α-GalCer (α-galactsylceramide), α-C-GalCer (α-C-galactsylceramide), iGB3 (isoglobotrihexosylceramide), GD3 (ganglioside 3), GSL-1 (α-linked glucronic acid), and GSL-1'SA (galacturonic acid). Among those glycolipids, α-GalCer or α-C-GalCer is preferable.

Further, the cell of the present invention is preferably an established cell line. The established cell line is high in proliferation efficiency and gene introduction efficiency, as compared with a cell or the like obtained from a living body. Therefore, from the established cell line, it is possible to stably prepare a large amount of cells. The established cell line can be a mammal-derived cell. In view of clinical application to a human, the cell of the present invention is preferably a human-derived cell, especially, a cell derived from a normal cell of a human. Note that, in a case of application to a pet animal (such as a dog and a cat), a cell derived from an animal species which is a target of administration can be used. Alternatively, a human-derived cell can be used therefor as with the application to a human.

Nucleic Acid Construct of the Present Invention

Further, the present invention provides a nucleic acid construct encoding a Wilms tumor gene product or a fragment of the Wilms tumor product and enhancing an expression level of the Wilms tumor gene product or the fragment of the Wilms tumor gene product. As described above, the nucleic acid construct includes (i) a region encoding a fragment of the Wilms tumor gene product, the fragment being indicated by positions 194 to 493 of SEQ ID NO: 1 or by positions corresponding to the positions 194 to 493 of a sequence corresponding to SEQ ID NO: 1 and (ii) only one AUG as a functional start codon, connected to a 5' terminal side of the region via 3m (m is 0 or a positive integer) bases intervening between the 5' terminal side of the region and the AUG as the functional start codon.

Each of the terms "Wilms tumor gene product" and "fragment of the Wilms tumor gene product" used in the present specification means (i) a polypeptide represented by an amino acid sequence identical to that of a wild type protein encoded by a Wilms tumor gene (Wilms tumor 1: WT1) (hereinafter, referred to as a "polypeptide identical to a wild type protein"), (ii) a polypeptide represented by an amino acid sequence substantially identical to that of the wild type protein (hereinafter, referred to as a "polypeptide similar to a wild type protein"), or (iii) a polypeptide containing a WT1-derived peptide, which is known as a tumor-specific antigen peptide (hereinafter, referred to as a "tumor-specific polypeptide").

Note, here, that the polypeptide identical to a wild type protein is a polypeptide encoded by cDNA of a publicly-known WT1 gene. The WT1 gene has various variants. Among the variants, cDNA encoding a polypeptide whose full length is the longest is represented by a sequence of SEQ ID NO: 3 (GenBank# NM_024426). What is represented by this sequence is known as Variant D of WT1. Currently, it is known that WT1 has Variants A through D (A: GenBank# NM 000378, B: GenBank# NM 024424, C: GenBank# NM 024425, D: GenBank# NM 024426). The polypeptide identical to a wild type protein in the present specification means, for example, a polypeptide encoded by a polynucleotide represented by a sequence of SEQ ID NO: 3 in which substitution, deletion, or addition each being observed in various variants is optionally introduced into a corresponding position thereof. Note that the WT1 gene is known to express two proteins having respective different lengths. Therefore, the term "polypeptide identical to a wild type protein" includes a polypeptide which has or does not have the mutation observed in the variants as those described above and which is represented by an amino acid sequence identical to those of two proteins having the respective different lengths.

On the other hand, in comparison with the polypeptide identical to a wild type protein in terms of an amino acid sequence, the polypeptide similar to a wild type protein is a polypeptide having an amino acid sequence with 90% or more, preferably 95% or more, more preferably 99% or more identity to that of the polypeptide identical to a wild type protein. Furthermore, the polypeptide similar to a wild type protein is a polypeptide having a region corresponding to a tumor-specific antigen peptide into which a mutation being known not to impair immune inducibility, being known to improve immune inducibility, or being known to change an applicable type of a human leukocyte antigen is introduced.

Examples of the mutation include a mutation described in WO 05/045027. The mutation is substitution of an amino acid at position 1, 4, 6, or 9 from a C-terminal of a peptide consisting of nine amino acid residues with another amino acid. In accordance with WO 05/045027, an amino acid residue can be substituted with another amino acid according to the following correspondence: An amino acid at position 1 can be substituted with any one of phenylalanine, tyrosine, tryptophan, valine, isoleucine, leucine, and methionine. An amino acid at position 4 can be substituted with any one of valine, isoleucine, leucine, methionine, aspartic acid, and glutamic acid. An amino acid at position 6 can be substituted with any one of asparagine, serine, threonine, glutamine, lysine, and aspartic acid. An amino acid at position 9 can be substituted with aspartic acid, glutamic acid, or glutamine.

Examples of the mutation further include a mutation described in WO 05/053618. According to the mutation, an amino acid at position 9 of nine amino acid residues encoded by bases corresponding to bases at positions 770 to 796 of SEQ ID NO: 3 of the present invention is substituted with leucine.

Examples of the mutation further include a mutation described in WO 07/016466. According to the mutation, an amino acid at position 9 of nine amino acid residues encoded by bases corresponding to bases at positions 770 to 796 of SEQ ID NO: 3 of the present invention is substituted with methionine.

Examples of the mutation further include two mutations described in a Response of European patent No. 1127068. According to a first one of the two mutations, an amino acid at position 2 of nine amino acid residues encoded by bases corresponding to bases at positions 770 to 796 of SEQ ID NO: 3 of the present invention is substituted with leucine. According to a second one of the two mutations, amino acids at positions 2 and 9 of nine amino acid residues encoded by bases corresponding to bases at positions 770 to 796 of SEQ ID NO: 3 of the present invention are substituted with leucine and valine, respectively.

On the other hand, in comparison with the polypeptide identical to a wild type protein in terms of an amino acid sequence of a region containing an antigen peptide, the tumor-specific polypeptide is a polypeptide having an amino acid sequence with 90% or more, preferably 95% or more, more preferably 99% or more identity to that of the polypeptide identical to a wild type protein. Furthermore, the polypeptide similar to a wild type protein is a polypeptide into which a mutation being known not to impair immune inducibility, being known to improve immune inducibility, or being known to change an applicable type of a human leukocyte antigen is introduced. Examples of the mutation include the mutations described above.

Thus, the nucleic acid construct of the present invention contains a polynucleotide encoding the polypeptide identical to a wild type protein, the polypeptide similar to a wild type protein, or the tumor-specific peptide. Therefore, in addition to the mutation in the WT1 gene as those described above, the nucleic acid construct of the present invention optionally has a conservative mutation which does not change an amino acid to be encoded.

Into the nucleic acid construct of the present invention, such a mutation is further introduced by which one or two base(s) is/are inserted into a 5' terminal side of "A" at the beginning thereof, in a case where (i) bases represented by "AUG" are generated, by any of the aforementioned mutations, at any position in a region from positions 192 to 769 of SEQ ID NO: 2 or in a region corresponding to that region of a sequence corresponding to SEQ ID NO: 2 and (ii) "A" at the beginning thereof exists at a position other than positions 191+3n (n is an integer from 1 to 192).

As used in the present specification, the term "corresponding sequence" in the descriptions referring to SEQ ID NO: 2 means a sequence of RNA corresponding to publicly-known cDNA indicating any of the various the variants of the WT1 gene as those described above, into which variants any of the various mutations can be introduced as described above. Further, the term "corresponding base" means a base specified in the "corresponding sequence" when compared with a base at position X (X is any integer) of SEQ ID NO: 2 and bases around that base. A person skilled in the art who reads the present specification would easily understand the meanings of the terms "corresponding sequence" and "corresponding base", and easily find out, in a suitably-selected "corresponding sequence" of SEQ ID NO: 2, a "corresponding base" of the base at the position X of SEQ ID NO: 2. Hereinafter, the nucleic acid construct of the present invention will be explained with reference to SEQ ID NO: 2, which is shown as a reference sequence. Further, in all the descriptions, the nucleic acid construct of the present invention is intended to be indicated by a position or a region of a base in a sequence corresponding to SEQ ID NO: 2.

In the nucleic acid construct of the present invention, a base corresponding to a base at position 191 of SEQ ID NO: 2 can be substituted with a base represented by, for example, "A", "U", or "G". It has been reported that such the substitution with any of "A", "U", and "G" can generate a codon serving as a start codon in a eukaryote. Further, in the nucleic acid construct of the present invention, any successive bases from a base corresponding to a base at position 191 of SEQ ID NO: 2 to a base at position 769 of SEQ ID NO: 2 can be deleted. This makes it possible to provide a nucleic acid construct encoding a polypeptide which contains a publicly-known tumor-specific antigen peptide as those described above.

Preferably, into the nucleic acid construct of the present invention, such a mutation is introduced that generates a region starting from three bases represented by "AUG". This mutation generates a start codon which is found in eukaryotes the most, thereby increasing the possibility that this region is recognized as a coding region, so as to enhance an expression level of a polypeptide encoded by the nucleic acid construct of the present invention. Examples of RNA contained in the nucleic acid construct to which such a mutation is introduced include the following three RNAs:

RNA (1) represented by SEQ ID NO: 2 in which a base at position 191 is substituted with "A"; RNA (2) represented by SEQ ID NO: 2 in which successive 204 bases starting from a base at position 191 are deleted; and RNA (3) containing (i) a first region in which three bases represented by "AUG" and any 3m (m is an integer of 0 (zero) or 1 to 250, more preferably 1 to 200) bases are positioned continuously in this order from a 5' terminal and (ii) a second region from position 770 to position 1663 of SEQ ID NO: 2, the first region being followed by the second region.

The RNA (1) is RNA including a region of the nucleic acid construct of the present invention which region encodes a WT1 polypeptide and has the first base being substituted with a base represented by "A". The RNA (2) is RNA including a region of the nucleic acid construct of the present invention which region encodes a WT1 polypeptide and starts from three bases represented by "AUG". The RNA (3) is RNA including (i) "AUG", (ii) 0 (zero) or 3-multiple bases positioned to follow the "AUG", and (iii) a polypeptide chain including a region identified to encode a tumor-specific antigen peptide (a region from a position 770 to a position 1663 of SEQ ID NO: 2), the "AUG" and the 0 (zero) or 3-multiple bases being added to a C-terminal of the polypeptide chain. With any of the RNAs (1) to (3), it is possible to obtain RNA which expresses the Wilms tumor gene product or the fragment of the Wilms tumor gene product in a considerably enhanced level as compared with a wild type.

Further, the nucleic acid construct of the present invention is preferably the one represented by (i) SEQ ID NO: 2 in which bases at positions 1 to 100, preferably positions 1 to 150, more preferably 1 to 120, even more preferably positions 1 to 190 of SEQ ID NO: 2 are deleted or (ii) the corresponding sequence in which bases corresponding to these bases are deleted. In a case where the nucleic acid construct, having such the deletion, of the present invention is inserted into a transcription construct (described later), a protein is expressed more suitably because a distance between a promoter and a start codon is suitably adjusted therein.

Note here that an expression level of the protein from the nucleic acid construct of the present invention is at least 5 times or more, preferably 25 times or more as high as that of a wild type. In a case where the nucleic acid construct of the present invention is introduced into a cell, use of a small amount of such cells makes it possible to prepare a necessary amount of proteins. Particularly, in a case where such a cell is administered to a living body, use of a small amount of such cells makes it possible to provide the living body with proteins whose amount is sufficient to induce a desired response to the living body. Thus, with the nucleic acid construct of the present invention, it is possible to significantly reduce troublesome procedures involved in preparing such cells homogeneously and in a large amount, thereby making it possible to administer the cells to a living body more easily. As described later in Examples, the present invention is capable of providing the nucleic acid construct by which an expression level of a protein is enhanced by approximately 50 times or more at a maximum as compared with a case of using a wild type. Therefore, the nucleic acid construct of the present invention is far easy to handle and is extremely useful as compared with a wild type.

The nucleic acid construct of the present invention preferably includes a region indicated by SEQ ID NO: 4 or 5

(effectiveness attained thereby will be described in Examples). With the nucleic acid construct of the present invention including that region, an expression level of a protein can be enhanced by 25 times or more as compared with a case of using a wild type.

Furthermore, the nucleic acid construct of the present invention preferably includes a 5' cap structure. The 5' cap structure in the nucleic acid construct of the present invention can be added in vitro or in vivo. In consideration of facilitation of purification and isolation, it is preferable that (i) transcription is carried out in vitro with the use of RNA including a region encoding a WT1 polypeptide and (ii) the 5' cap structure is then added thereto in vitro. The transcription and the addition of the 5' cap structure in vitro can be easily carried out by a method publicly known to a person skilled in the art, or with the use of a commercially available reagent or kit.

Furthermore, in order to improve stability of RNA and an expression level of a protein, it is preferable that the nucleic acid construct of the present invention further includes a polyadenylation (Poly-A) chain at its 3' terminal. The Poly-A chain can be added to the nucleic acid construct of the present invention in vitro or in vivo as with the 5' cap structure. However, for similar reasons, it is preferable that the Poly-A chain is added to the nucleic acid construct of the present invention in vitro. Similarly, the addition of the Poly-A chain can be easily carried out by a method publicly known to a person skilled in the art, or with the use of a commercially available reagent or kit.

Polynucleotide Encoding Nucleic Acid Construct of the Present Invention, and Transcription Construct Containing the Polynucleotide The present invention provides a polynucleotide encoding the nucleic acid construct of the present invention as described above. The polynucleotide of the present invention includes a region of a WT1 gene encoding a WT1 gene product or a fragment of the WT1 gene product. Further, into the polynucleotide, such a mutation is introduced that corresponds to the mutation introduced into the nucleic acid construct of the present invention as described above. The polynucleotide of the present invention is particularly suitable for production of the nucleic acid construct of the present invention. In a case where the polynucleotide is used to produce the nucleic acid construct of the present invention, the polynucleotide of the present invention is incorporated into a transcription construct of the nucleic acid construct of the present invention.

As described above, the present invention also provides a transcription construct containing the polynucleotide of the present invention. The transcription construct further contains various elements which enable efficient transcription of the polynucleotide to RNA. As described above, the transcription of the nucleic acid construct of the present invention is preferably carried out in vitro. Therefore, the various elements to be contained in the transcription construct can be selected in accordance with a method, a kit, or the like for in vitro transcription. The following description will specifically discuss, as an example of the transcription construct of the present invention, a construct adapted to a commercially available kit for in vitro transcription.

The transcription construct contains a promoter which is operably linked to the polynucleotide. The promoter is applicable as long as the promoter can promote the transcription of the polynucleotide to RNA in vitro. Examples of the promoter include a T7 promoter, an SP6 promoter, and a T3 promoter. The transcription construct can further contain a transcription termination signal (that is, a terminator sequence) at a downstream of the polynucleotide. Examples of the terminator sequence include a T7 terminator, an SP6 terminator, and a T3 terminator. Note that the transcription termination signal is not necessary, in a case where transcription is carried out after the transcription construct is cut out at a downstream of the polynucleotide by use of a restriction enzyme or the like.

The transcription construct can function as a vector so as to amplify the transcription construct itself. In this case, the transcription construct can further contain a selection marker gene for selection of a cell into which the transcription construct is introduced. Examples of the selection marker gene include a gene having resistance to a conventionally known antibiotic, a gene which compensates for an auxotrophic mutation, and a gene which expresses an enzyme that catalyzes a color reaction with a reagent. In a case where the transcription construct does not have such selectivity, the transcription construct can be amplified by PCR, for example. Therefore, the transcription construct can be a linear polynucleotide chain which is amplified by PCR and which is not inserted into plasmid DNA. In this case, a primer pair is designed so that a template is amplified together with a promoter region of RNA.

In a case where a transcription construct further encoding mRNA of CD1d is prepared, the transcription construct is polycistronic or monocistronic. In a case where the transcription construct is polycistronic, the transcription construct contains one promoter at an upstream of two coding regions. In a case where the transcription construct is monocistronic, the transcription construct contains one promoter at an upstream of each coding region. Alternatively, of course, two transcription constructs can be prepared, that is, one for the nucleic acid construct of the present invention and the other for mRNA of CD1d. In addition to these aspects, such an aspect is possible that a WT1 gene product and CD1d are expressed as a fusion protein. This aspect provides mRNA having a specific proteolytic signal sequence (such as a T2A sequence) between the WT1 gene product and CD1d. In a cell to which such mRNA is introduced, the fusion protein is expressed and then is degraded into two proteins, so as to exhibit activities as individual proteins.

Method for Producing Nucleic Acid Construct of the Present Invention

The nucleic acid construct of the present invention is produced by, for example, (i) a combination of amplification, cloning, and an in vitro transcription reaction of the polynucleotide encoding the nucleic acid construct or (ii) a publicly known technique such as chemical synthesis. The following description will discuss an example of a method for producing the nucleic acid construct of the present invention.

Such a primer pair is designed that can introduce a desired mutation into cDNA of a publicly known WT1 gene. The primer pair is designed so that, for example, an N terminal of a sequence of a wild type is deleted. In this case, normally, it is not necessary to adjust the number of bases to be deleted. This is because that RNA to be transcribed in vitro does not cause a frame-shift mutation, unless a mutation as those described in [Nucleic acid construct of the present invention] occurs. By determining a sequence of template cDNA to be used, it is possible to know whether or not a frame-shift mutation has occurred therein. Therefore, before use of the template DNA, the sequence of the template DNA may be determined in accordance with a publicly known method.

A desired polynucleotide is amplified by PCR using the primer pair and the template cDNA. The polynucleotide thus amplified and a vector used for cloning are digested by use of the same restriction enzyme. The vector and polynucleotide thus digested are ligated by use of a ligase, so that the vector (transcription construct) containing the polynucleotide is obtained.

By use of the vector containing the polynucleotide of the present invention, for example, suitable *Escherichia coli* is transformed. The *Escherichia coli* thus transformed is then grown in a suitable culture medium. The vector contains, for example, a specific antibiotic resistance gene, and the culture medium used to grow the *Escherichia coli* contains the specific antibiotic. The vector is extracted from a bacterial cell with the use of a commercially available kit or the like.

The vector thus extracted is subjected to an in vitro transcription reaction with the use of a commercially available kit, with the vector being kept circular or being processed to be linear. In a case where a resulting transcription product does not have a modification such as a cap structure added to a 5' terminal and a Poly-A sequence added to a 3' terminal, the cap structure can be added to the 5' terminal of the transcription product and the poly A sequence can be added to the 3' terminal of the transcription product with the use of a commercially available kit.

The above description has given a simple discussion mainly on the method for producing the nucleic acid construct of the present invention with the use of a kit. However, a person skilled in the art would understand that he/she can prepare by himself/herself part of the reagents used to produce the nucleic acid construct. Therefore, a person skilled in the art can produce more suitable RNA by partially altering a commercially available kit or by changing part of the reagents in accordance with a nature of RNA to be produced. Particularly, with reference to Examples described later, a person skilled in the art would sufficiently understand a technique suitable to produce the nucleic acid construct of the present invention, a reagent to be prepared, a kit to be selected, and part of those which should be changed.

Kit for Producing Cell for Immunotherapy of the Present Invention

The present invention further provides a kit for producing the cell for immunotherapy. The kit includes the aforementioned nucleic acid construct or polynucleotide. In a case where the kit includes the nucleic acid construct of the present invention, a user introduces the nucleic acid construct into a cell described in [Cell for immunotherapy of the present invention] with the use of the kit. In a case where the kit includes the polynucleotide of the present invention (as the transcription construct), the user obtains the nucleic acid construct of the present invention as a result of in vitro or in vivo transcription of the polynucleotide, and then introduces the nucleic acid construct into a cell. The kit can further include an instruction manual. The instruction manual includes information necessary for producing the cell for immunotherapy (the nucleic acid construct, as necessary) of the present invention, for example, information that can be understood from the descriptions made so far in the present specification.

To sum up, the present invention includes the following features in order to attain the above object:

(1) a cell for immunotherapy, including: a nucleic acid construct encoding a Wilms tumor gene product or a fragment of the Wilms tumor gene product, the nucleic acid construct including (i) a region encoding a fragment of the Wilms tumor gene product, the fragment being indicated by positions 194 to 493 of SEQ ID NO: 1 or by positions corresponding to the positions 194 to 493 of a sequence corresponding to SEQ ID NO: 1 and (ii) only one AUG as a functional start codon, connected to a 5' terminal side of the region via 3m (m is 0 or a positive integer) bases intervening between the 5' terminal side of the region and the AUG as the functional start codon;

(2) the cell as set forth in (1), wherein: as the region encoding the fragment of the Wilms tumor gene product, the nucleic acid construct includes a region encoding a fragment of the Wilms tumor gene product, the fragment being indicated by positions 69 to 517 of SEQ ID NO: 1 or by positions corresponding to the positions 69 to 517 of a sequence corresponding to SEQ ID NO: 1; and the nucleic acid construct is such that all of CUG at positions 191 to 193 are deleted or C of CUG at positions 191 to 193 is substituted with A in the sequence indicated by SEQ ID NO: 2;

(3) the cell as set forth in (1) or (2), wherein a production amount of proteins directly translated from the nucleic acid construct is 25 times or more as large as that of proteins directly translated from RNA including a coding region indicated by positions 191 to 1741 of SEQ ID NO: 2;

(4) a nucleic acid construct for producing a cell recited in any one of (1) through (3), the nucleic acid construct being directly translated into a protein in a cell into which the nucleic acid construct is introduced;

(5) the nucleic acid construct, including a region indicated by SEQ ID NO: 4 or 5;

(6) a method for producing a cell for immunotherapy, including the step of introducing, into a cell, a nucleic acid construct recited in (4) or (5);

(7) a polynucleotide encoding a nucleic acid construct recited in (4) or (5);

(8) a kit for producing a cell for immunotherapy, including a nucleic acid construct recited in (4) or (5), or a polynucleotide recited in (7); and (9) the cell as set forth in any one of (1) through (3), further including mRNA encoding CD1d, the CD1d existing on a surface of the cell and being bound to a glycolipid recognizable by an antigen receptor of an NKT cell.

EXAMPLES

The following description will discuss (i) an example of a method for preparing RNA of the present invention and (ii) results of comparison of the amounts of proteins translated from the RNAs with that from a wild type RNA. The Examples are only shown to illustrate the present invention, and do not limit the scope of the present invention.

Cloning of Polynucleotide Encoding RNA of the Present Invention

A polynucleotide sequence of a target WT1 was obtained by PCR. Used as a template was plasmid DNA into which purchased cDNA (#SC308799, OriGene Technologies, SEQ ID NO: 3) encoding Variant D of human WT1 was inserted. Used as DNA polymerase for PCR was KOD-Plus-Ver.2 (#KOD-211, Toyobo Co., Ltd.). Oligonucleotide sequences of a primer pairs and a reaction condition of PCR were as follows.

(Primer Pair for ATG-WT1)
Forward: 5'-CCAAGCTTCCACCATGCAGGACCCG-GCTTCCACG-3' (SEQ ID NO: 6, Positions 3 to 8: a recognition sequence of the restriction enzyme HindIII; Positions 9 to 13: Kozak sequence; Positions 14 to 34: part of coding region sequence of WT1);
Reverse: 5'-CGGAATTCTCAAAGCGCCAGCTG-GAGTTTGG-3' (SEQ ID NO: 7, Positions 3 to 8: a recognition sequence of the restriction enzyme EcoRI; Positions 9 to 31: part of coding region sequence of WT1).

(Primer Pair for ΔN-WT1)
Forward: 5'-CCAAGCTTCCACCATGGGCTCCGACGT-GCGGGA-3' (SEQ ID NO: 8, Positions 3 to 8: a recognition sequence of the restriction enzyme HindIII; Positions 9 to 13: Kozak sequence; Positions 14 to 33: part of coding region sequence of WT1);
Reverse: 5'-CGGAATTCTCAAAGCGCCAGCTG-GAGTTTGG-3' (SEQ ID NO: 9, Positions 3 to 8: a recognition sequence of the restriction enzyme EcoRI; Positions 9 to 31: part of coding region sequence of WT1).

TABLE 1

(Composition of Reaction Solution for PCR)

| Water | 25.6 µl |
|---|---|
| 10× Buffer for KOD-Plus-Ver. 2 | 4.0 µl |
| 2 mM dNTPs | 4.0 µl |
| 25 mM MgSO4 | 2.4 µl |
| Forward primer (10 µM) | 1.2 µl |
| Reverse primer (10 µM) | 1.2 µl |
| WT1 cDNA (1 ng/µl) | 0.8 µl |
| KOD-Plus-(1 U/µl) | 0.8 µl |
| Total | 40.0 µl |

TABLE 2

(Reaction Condition of PCR)

| #1 | 94° C., 2 minutes |
|---|---|
| #2 | 98° C., 10 seconds |
| #3 | 60° C., 30 seconds |
| #4 | 68° C., 1 minute and 30 seconds |
| #5 | #2-#4 × 29 (total: 30 cycles) |
| #6 | 4° C. (continued) |

An expected chain length of the amplification products of ATG-WT1 (corresponding to positions 191 to 1741 ("c" at position 191 was substituted with "a") of SEQ ID NO: 3) as the result of PCR was approximately 1580 base pairs, and an expected chain length of the amplification products of ΔN-WT1 (corresponding to positions 395 to 1741 of SEQ ID NO: 3) as the result of PCR was approximately 1350 base pairs. By agarose gel electrophoresis, it was confirmed that the chain lengths of those PCR products did not conflict with theoretical values. Those amplification products were cloned into the plasmid pcDNA3, and the plasmids thus obtained were named pcDNA3-ATG-WT1 and pcDNA3-ΔN-WT1, respectively.

(Production of Synthetic RNA of the Present Invention)

The plasmids (pcDNA3-ATG-WT1 and pcDNA3-ΔN-WT1) were processed to be linear by use of the restriction enzyme NotI (recognition sequence is on pcDNA3). Each of the linear plasmids thus obtained was purified by use of QIAquick PCR Purification Kit (#28106, Qiagen) and then used as a template for RNA synthesis. As a result, desired RNAs were synthesized.

(Determination of Expression Levels of Protein from Mutant RNAs of the Present Invention)

The two mutant WT1 mRNAs were compared with wild type WT1 mRNA in terms of protein expression level.

HEK293 ($3 \times 10^6$ cells) were plated on three dishes, and were transfected with an identical amount of each of the two mutant WT1 mRNAs and the wild type WT1 mRNA by a lipofection method. The cells thus transfected in each dish were incubated in a $CO_2$ incubator at 37° C. Then, after the culture medium was removed from each dish, a lysis buffer for electrophoresis was added. Thereafter, the cells thus incubated were collected from each dish with the use of a cell scraper, and then were moved into a tube. The cell lysate in each tube was then homogenized by sonication, and samples for electrophoresis were obtained.

Each of the samples was diluted as appropriate, and 15 µl of each of the samples was then electrophoresed (a dilution ratio of each of the samples will be described later). Then, each gel was equilibrated, and each of the samples was transferred from the gel to a membrane. The membranes to which the respective samples were transferred were blocked, and then incubated together with rabbit anti-WT1 antibodies (SC-192, Santa Cruz Biotechnology, Inc.). The membranes were then washed three times, and incubated together with secondary antibodies, goat anti-rabbit IgG labeled with HRP (#HAF008, R&D systems, Inc.). The membranes were washed three times with TBS containing 0.05% Tween20. Thereafter, the membranes were processed with the use of Immobilon Western (#WBKLS0500, EMD Millipore Corporation), so that bands were detected.

FIG. 1 illustrates a detection result of the bands. A value before "×" shown above each lane indicates the dilution ratio of each sample applied to the polyacrylamide gel with respect to the original cell lysate. On the wild type WT1 mRNA, a full-length protein (517 amino acids) was detected as the major band, and a band shorter than the full-length protein was detected as the minor band (see "1×" and "5×" of CTG). On the WT1 RNA in which part of the N terminus was deleted, a protein was detected as a band having higher intensity by approximately 50 times or more than that of the minor bands of the wild type WT1 mRNA at the same position as that of the minor band of the wild type WT1 mRNA (see "25×" and "50×" of delta). Also on the WT1 RNA in which the first base in the coding region was substituted with "A", a protein was detected as a band having an intensity which was approximately 50 times or more as high as that of the major bands of the wild type WT1 mRNA at the same position as that of the major band of the wild type WT1 mRNA (see "25×" and "50×" of ATG).

Further, a band in std of 50 ng was detected. Comparison with the intensity of the band of std shows that the detected amount of the wild type WT1 mRNA was at least approximately 50 ng in the case of "1×". The volume of the applied sample corresponds to one-tenth of that of the original sample. Therefore, the expression level per 1×10⁶ cells was at least approximately 250 ng. This amount of protein is not sufficient to induce immunity in an animal having a weight of approximately 3 kg. On the other hand, each of the expression levels of WT1 from the two mutant RNAs (delta and AUG) was at least approximately 50 times or more as high as that of WT1 from the wild type WT1 mRNA. That is, each of the expression levels of WT1 per 1×10⁶ cells from the two mutant RNAs was approximately 30 μg or more.

INDUSTRIAL APPLICABILITY

The present invention is expected to be applied to the biological fields and the medical fields, particularly, to treatments for tumors.

The invention claimed is:

1. A human cell for antitumor immunotherapy, comprising:
a nucleic acid construct encoding a Wilms tumor gene product or a fragment of the Wilms tumor gene product, the nucleic acid construct including (i) a region encoding a fragment of the Wilms tumor gene product, the fragment being indicated by positions 194 to 493 of sequence NO:1 or by positions corresponding to the positions 194 to 493 of a sequence corresponding to SEQ ID NO:1 and (ii) only one AUG as a functional start codon, connected to a 5' terminal side of the region via 3m (m is 124-192) bases intervening between the 5' terminal side of the region and the AUG as the functional start codon.

2. The human cell as set forth in claim 1, wherein a production amount of proteins directly translated from the nucleic acid construct is 25 times or more as large as that of proteins directly translated from RNA including a coding region indicated by positions 191 to 1741 of SEQ ID NO:2.

3. A nucleic acid construct for producing a human cell recited in claim 1, the nucleic acid construct being directly translated into a protein in a human cell into which the nucleic acid construct is introduced.

4. A method for producing a human cell for antitumor immunotherapy, comprising the step of introducing, into a human cell, a nucleic acid construct recited in claim 3.

5. The human cell as set forth in claim 1, further comprising mRNA encoding CD1d, the CD1d existing on a surface of the human cell and being bound to a glycolipid recognizable by an antigen receptor of an NKT cell.

6. A method for performing an antitumor immunotherapy comprising inducing antitumor immunity in a target by administering a human cell recited in claim 1 to the target.

7. The human cell as set forth in claim 1, wherein the nucleic acid construct is generated in the human cell by means of transcription from a DNA.

* * * * *